US008882674B2

(12) United States Patent
Weinbaum et al.

(10) Patent No.: US 8,882,674 B2
(45) Date of Patent: Nov. 11, 2014

(54) SYSTEM AND METHOD FOR IN VIVO IMAGING OF BLOOD VESSEL WALLS TO DETECT MICROCALCIFICATIONS

(75) Inventors: Sheldon Weinbaum, Brooklyn, NY (US); Yuliya Vengrenyuk, Mamaroneck, NY (US); Luis Cardoso, New York, NY (US); Lucas Parra, New York, NY (US); Stephane Carlier, Flobecq (BE); Savvas Xanthos, Astona, NY (US)

(73) Assignees: Research Foundation of the City University of New York, New York, NY (US); Columbia University, New York, NY (US)

( * ) Notice: Subject to any disclaimer, the term of this patent is extended or adjusted under 35 U.S.C. 154(b) by 1291 days.

(21) Appl. No.: 11/861,181

(22) Filed: Sep. 25, 2007

(65) Prior Publication Data

US 2008/0091105 A1    Apr. 17, 2008

Related U.S. Application Data (60) Provisional application No. 60/848,027, filed on Sep. 28, 2006.

(51) Int. Cl.
| | |
|---|---|
| *A61B 8/00* | (2006.01) |
| *A61B 5/00* | (2006.01) |
| *A61B 8/12* | (2006.01) |
| *A61B 5/055* | (2006.01) |
| *A61B 6/03* | (2006.01) |

(52) U.S. Cl.
CPC ............... *A61B 8/12* (2013.01); *A61B 5/0084* (2013.01); *A61B 5/0066* (2013.01); *A61B 5/0073* (2013.01); *A61B 5/055* (2013.01); *A61B 5/0068* (2013.01); *A61B 5/0075* (2013.01); *A61B 6/03* (2013.01)
USPC ............ 600/443; 600/407; 600/437; 600/467

(58) Field of Classification Search
USPC ......................... 600/427, 424, 433–435, 407; 606/151–156, 189, 198; 128/898; 604/96, 104, 164; 623/1, 2
See application file for complete search history.

(56) References Cited

U.S. PATENT DOCUMENTS

| | | | | |
|---|---|---|---|---|
| 5,289,374 | A | * | 2/1994 | Doi et al. ...................... 600/407 |
| 5,709,206 | A | * | 1/1998 | Teboul .......................... 600/437 |

(Continued)

OTHER PUBLICATIONS

Imoto et al, "Longitudinal Structural Determinants of Atherosclerotic Plaque Vulnerability", Journal of the American College of Cardiology, vol. 46, No. 8, 2005.*

(Continued)

*Primary Examiner* — Nicholas Evoy
(74) *Attorney, Agent, or Firm* — Scully, Scott, Murphy & Presser, P.C.

(57) ABSTRACT

A system includes an in vivo imaging device for imaging a blood vessel with a resolution level of at least fifty micrometers. The in vivo imaging device is capable of detecting a microcalcification in a fibrous cap of an atheroma. The system also includes a processor for receiving an image of the blood vessel from the in vivo imaging device. The processor uses the image to determine whether the blood vessel contains at least one microcalcification within the fibrous cap. In some embodiments, the processor is configured and arranged to predict a risk of rupture of the fibrous cap based, at least in part, on the presence of the at least one microcalcification. In some embodiments, treatment of a patient is based on the determination from the imaging whether the blood vessel includes at least one microcalcification within the fibrous cap of the atheroma.

13 Claims, 5 Drawing Sheets

(56) References Cited

U.S. PATENT DOCUMENTS

| | | | | |
|---|---|---|---|---|
| 5,810,010 A * | 9/1998 | Anbar | | 600/474 |
| 5,830,141 A * | 11/1998 | Makram-Ebeid et al. | | 600/407 |
| 5,984,870 A * | 11/1999 | Giger et al. | | 600/443 |
| 5,997,477 A * | 12/1999 | Sehgal | | 600/437 |
| 6,035,225 A * | 3/2000 | Anbar | | 600/407 |
| 6,081,738 A * | 6/2000 | Hinohara et al. | | 600/407 |
| 6,122,542 A * | 9/2000 | Lee et al. | | 600/427 |
| 6,157,852 A * | 12/2000 | Selmon et al. | | 600/407 |
| 6,200,267 B1 * | 3/2001 | Burke | | 600/443 |
| 6,217,518 B1 * | 4/2001 | Holdaway et al. | | 600/443 |
| 6,241,667 B1 * | 6/2001 | Vetter et al. | | 600/407 |
| 6,317,617 B1 * | 11/2001 | Gilhuijs et al. | | 600/408 |
| 6,351,660 B1 * | 2/2002 | Burke et al. | | 600/425 |
| 6,385,474 B1 * | 5/2002 | Rather et al. | | 600/407 |
| 6,475,159 B1 * | 11/2002 | Casscells et al. | | 600/549 |
| 6,582,368 B2 * | 6/2003 | Holdaway et al. | | 600/443 |
| 6,615,071 B1 * | 9/2003 | Casscells et al. | | 600/474 |
| 6,692,430 B2 * | 2/2004 | Adler | | 600/109 |
| 6,692,439 B1 * | 2/2004 | Walker et al. | | 600/443 |
| 6,701,181 B2 * | 3/2004 | Tang et al. | | 600/478 |
| 6,714,808 B2 * | 3/2004 | Klimberg et al. | | 600/411 |
| 6,728,567 B2 * | 4/2004 | Rather et al. | | 600/407 |
| 6,763,261 B2 * | 7/2004 | Casscells et al. | | 600/474 |
| 6,780,159 B2 * | 8/2004 | Sandler et al. | | 600/504 |
| 6,816,743 B2 * | 11/2004 | Moreno et al. | | 600/473 |
| 6,855,114 B2 * | 2/2005 | Drukker et al. | | 600/443 |
| 6,984,210 B2 * | 1/2006 | Chambers et al. | | 600/443 |
| 6,993,382 B2 * | 1/2006 | Casscells et al. | | 600/545 |
| 7,077,812 B2 * | 7/2006 | Naghavi | | 600/587 |
| 7,806,827 B2 * | 10/2010 | Zhang et al. | | 600/459 |
| 8,109,878 B1 * | 2/2012 | O'Ruanaidh et al. | | 600/443 |
| 8,376,947 B2 * | 2/2013 | Rambod et al. | | 600/437 |
| 8,622,909 B1 * | 1/2014 | O'Ruanaidh et al. | | 600/437 |
| 2001/0029336 A1 * | 10/2001 | Teo | | 600/442 |
| 2001/0047134 A1 * | 11/2001 | Holdaway et al. | | 600/459 |
| 2003/0028114 A1 * | 2/2003 | Casscells et al. | | 600/474 |
| 2003/0032880 A1 * | 2/2003 | Moore | | 600/437 |
| 2003/0055307 A1 * | 3/2003 | Elmaleh et al. | | 600/1 |
| 2003/0064025 A1 * | 4/2003 | Yang et al. | | 424/9.6 |
| 2003/0065263 A1 * | 4/2003 | Hare et al. | | 600/439 |
| 2003/0125621 A1 * | 7/2003 | Drukker et al. | | 600/437 |
| 2003/0149368 A1 * | 8/2003 | Hennemann et al. | | 600/483 |
| 2003/0171691 A1 * | 9/2003 | Casscells et al. | | 600/549 |
| 2003/0220556 A1 * | 11/2003 | Porat et al. | | 600/407 |
| 2003/0220569 A1 * | 11/2003 | Dione et al. | | 600/443 |
| 2004/0082850 A1 * | 4/2004 | Bonner et al. | | 600/424 |
| 2004/0111016 A1 * | 6/2004 | Casscells et al. | | 600/310 |
| 2004/0122304 A1 * | 6/2004 | Duric et al. | | 600/407 |
| 2004/0122325 A1 * | 6/2004 | Chambers et al. | | 600/467 |
| 2004/0133094 A1 * | 7/2004 | Becker et al. | | 600/407 |
| 2004/0147806 A1 * | 7/2004 | Adler | | 600/109 |
| 2004/0147840 A1 * | 7/2004 | Duggirala et al. | | 600/437 |
| 2004/0176686 A1 * | 9/2004 | Hare et al. | | 600/431 |
| 2004/0181152 A1 * | 9/2004 | Zhang et al. | | 600/437 |
| 2004/0254463 A1 * | 12/2004 | Lehman | | 600/437 |
| 2004/0254503 A1 * | 12/2004 | Sarvazyan et al. | | 600/587 |
| 2004/0260180 A1 * | 12/2004 | Kanai et al. | | 600/449 |
| 2005/0004467 A1 * | 1/2005 | Shiina et al. | | 600/449 |
| 2005/0014995 A1 * | 1/2005 | Amundson et al. | | 600/105 |
| 2005/0033141 A1 * | 2/2005 | Collins et al. | | 600/407 |
| 2005/0043614 A1 * | 2/2005 | Huizenga et al. | | 600/427 |
| 2005/0049495 A1 * | 3/2005 | Sumanaweera et al. | | 600/437 |
| 2005/0049497 A1 * | 3/2005 | Krishnan et al. | | 600/437 |
| 2005/0054924 A1 * | 3/2005 | Dione et al. | | 600/437 |
| 2005/0065426 A1 * | 3/2005 | Porat et al. | | 600/407 |
| 2005/0075574 A1 * | 4/2005 | Furnish et al. | | 600/467 |
| 2005/0119536 A1 * | 6/2005 | Hageman | | 600/300 |
| 2005/0148853 A1 * | 7/2005 | Redel | | 600/407 |
| 2005/0171430 A1 * | 8/2005 | Zhang et al. | | 600/437 |
| 2005/0182324 A1 * | 8/2005 | Angelsen et al. | | 600/437 |
| 2005/0203434 A1 * | 9/2005 | Kassab | | 600/547 |
| 2005/0277835 A1 * | 12/2005 | Angelsen et al. | | 600/437 |
| 2006/0032508 A1 * | 2/2006 | Simpson | | 128/898 |
| 2006/0036167 A1 * | 2/2006 | Shina | | 600/433 |
| 2006/0052699 A1 * | 3/2006 | Angelsen et al. | | 600/437 |
| 2006/0058592 A1 * | 3/2006 | Bouma et al. | | 600/301 |
| 2006/0058622 A1 * | 3/2006 | Tearney et al. | | 600/407 |
| 2006/0094980 A1 * | 5/2006 | Casscells et al. | | 600/549 |
| 2006/0206028 A1 * | 9/2006 | Lee et al. | | 600/471 |

OTHER PUBLICATIONS

Vengrenyuk, Yuliya et al., "A Hypothesis for Vulnerable Plaque Rupture Due to Stress-Induced Debonding Around Cellular Microcalcifications in Thin Fibrous Caps," PNAS, Oct. 3, 2006, vol. 30, No. 40, pp. 1-6.

Appendix A: Stresses and Displacements in a Fibrous Cap Containing a Perfectly Bonded Rigid Spherical Inclusion, 10 pgs.

* cited by examiner

SYSTEM AND METHOD FOR IN VIVO IMAGING OF BLOOD VESSEL WALLS TO DETECT MICROCALCIFICATIONS

CROSS-REFERENCE TO RELATED APPLICATIONS

This application claims priority from U.S. Ser. No. 60/848,027, filed Sep. 28, 2006, which is hereby incorporated by reference in its entirety.

TECHNICAL FIELD

The present invention is directed to systems for imaging blood vessel walls to predict the risk of fibrous cap rupture and methods of using the systems. The present invention is also directed to systems that include imaging blood vessel walls to identify microcalcifications, as well as methods of using the systems.

BACKGROUND OF THE INVENTION

Atherosclerosis is a disease affecting arterial blood vessels. Over time, arterial walls may respond to the deposition of lipoproteins by undergoing an inflammatory response and forming plaques, or atheromas. Atheromas can eventually lead to the occlusion of blood vessels by either swelling to a sufficient size to occlude a blood vessel or by rupturing and causing a downstream occlusion. Blood vessel occlusion may lead to morbidity and death of tissues left undernourished and/or oxygen starved. Consequently, many different possible acute health problems may arise, depending on the location of the occlusion, including some life-threatening conditions, such as ischemic stroke, myocardial infarction, and other cardiovascular diseases. Because of the many potential health risks involved with atheromas, health care professionals have invested large amounts of time and money into investigating atheromas with the eventual goal of either preventing the occurrence of atheromas or diagnosing already-formed atheromas prior to the potential occlusion of blood vessels. Unfortunately, the risk of rupture of an atheroma is often not known. Additionally, atheromas can remain asymptomatic for many years and may remain asymptomatic until a blood vessel has already become occluded.

BRIEF SUMMARY OF THE INVENTION

One embodiment is a method for detecting microcalcifications by imaging a portion of a blood vessel of a patient in vivo. The in vivo imaging is used to determine whether the blood vessel includes at least one microcalcification within a fibrous cap of an atheroma.

Another embodiment is a system that includes an in vivo imaging device for imaging a blood vessel with a resolution level of at least fifty micrometers. The in vivo imaging device is capable of detecting a microcalcification in a fibrous cap of an atheroma. The system also includes a processor for receiving an image of the blood vessel from the in vivo imaging device. The processor uses the image to determine whether the blood vessel contains at least one microcalcification within the fibrous cap.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION OF THE INVENTION

The present invention is directed to systems for imaging blood vessel walls to predict the risk of fibrous cap rupture and methods of using the systems. The present invention is also directed to systems that include imaging blood vessel walls to identify microcalcifications, as well as methods of using the systems.

Suitable medical diagnostic systems include, but are not limited to, in vivo imaging techniques for imaging a portion of a blood vessel of a patient to observe calcified inclusions ("microcalcifications") in a fibrous cap ("cap") of an atheroma. The term "microcalcification" refers to a calcified inclusion with a diameter of fifty micrometers or less. For example, a microcalcification diameter may be up to fifty micrometers, up to forty micrometers, up to twenty-five micrometers, up to twenty micrometers, between five micrometers and fifty micrometers, between five micrometers and forty micrometers, between five micrometers and twenty-five micrometers, and between ten micrometers and twenty micrometers.

Figure 1:
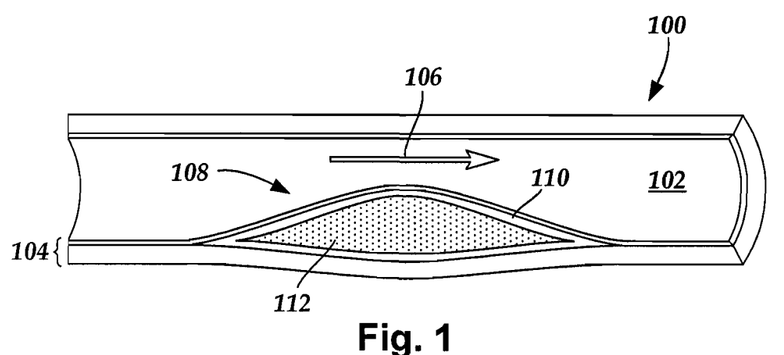
FIG. 1 is a is a schematic longitudinal cross-section of a portion of a blood vessel with an exemplary atheroma.

High-risk, or vulnerable, coronary atheroma prone to rupture or erosion are often a positively remodeled lesion rich in vasa-vasorium, containing a lipid-rich core ("core") with an overlying thin cap infiltrated by macrophages. FIG. 1 is a schematic longitudinal cross-section of a portion of a blood vessel with an exemplary atheroma. A blood vessel 100 includes a lumen 102, a wall 104 with multiple layers of tissue, and blood flowing through the lumen 102 generally in the direction indicated by directional arrow 106. The blood vessel 100 further includes an atheroma 108 between several layers of tissue in the wall 104. The atheroma 108 includes a cap 110 and a core 112. Caps typically include one or more layers of fibrous connective tissue and cores typically include many different types of materials, including macrophages, fatty cells, lipid-rich materials, cholesterol, calcium, foam cells, and the like.

Figure 2:
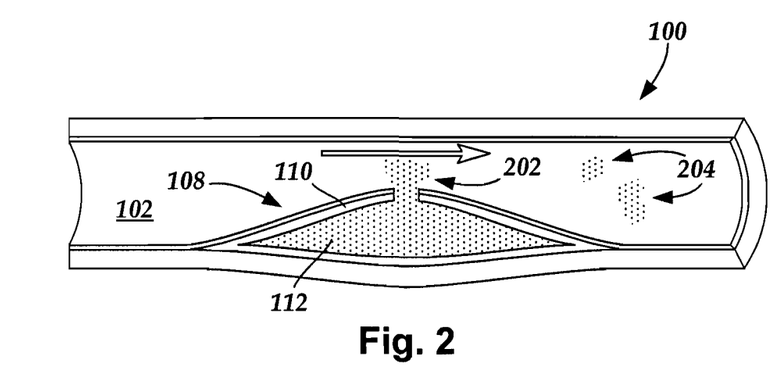
FIG. 2 is a is a schematic longitudinal cross-section of the portion of the blood vessel shown in FIG. 1 with an atheroma with a ruptured fibrous cap.

FIG. 2 is a schematic longitudinal cross-section of the portion of the blood vessel shown in FIG. 1 with an atheroma with a ruptured cap. In FIG. 2, the cap 110 has ruptured, exposing the core 112 of the atheroma 108 to the lumen 102 of the blood vessel 100. When a cap ruptures, pieces of the core can exit the atheroma and enter the lumen of the blood vessel. For example, in FIG. 2, a portion 202 of the core 112 is extending through the ruptured cap 110 and separated pieces 204 of the core 112 are shown downstream from the atheroma 108. Separated pieces 204 of the core 112 can be transported downstream and subsequently occlude the blood vessel 100 downstream from the atheroma 108, or occlude one or more other blood vessels downstream from the blood vessel 100.

Figure 3A:
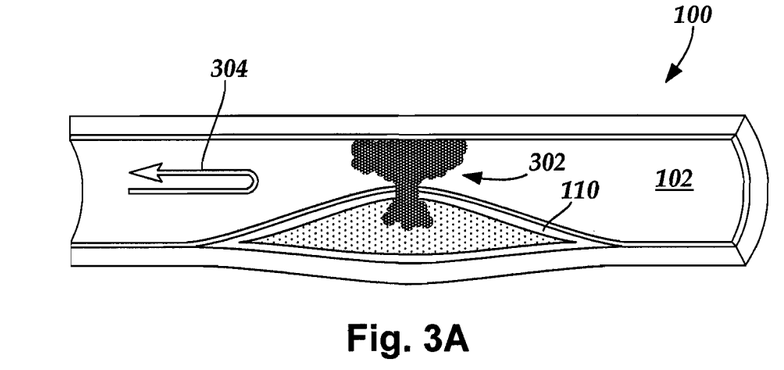
FIG. 3A is a is a schematic longitudinal cross-section of the portion of the blood vessel shown in FIG. 1 with an occluding thrombus formed in a fibrous cap rupture.

Thrombus formation may be triggered as a result of the cap rupture. FIG. 3A is a schematic longitudinal cross-section of the portion of the blood vessel shown in FIG. 1 with an occluding thrombus formed in a cap rupture. In FIG. 3A, a thrombus 302 has formed in and around the rupture of the cap 110. Sometimes a thrombus can form that is large enough to occlude a blood vessel. In FIG. 3A, the thrombus 302 has filled the rupture of the cap 110 and has expanded to occlude the lumen 102 of the blood vessel 100. In some cases, an occluding thrombus can halt the flow of blood downstream from the thrombus, as shown in FIG. 3A by U-shaped directional arrow 304. Pooling of blood may occur upstream from the atheroma which may cause many different ill-effects, such as development of an aneurism, or a tear in the wall of the blood vessel with or without subsequent internal bleeding and additional thrombus formation.

Figure 3B:
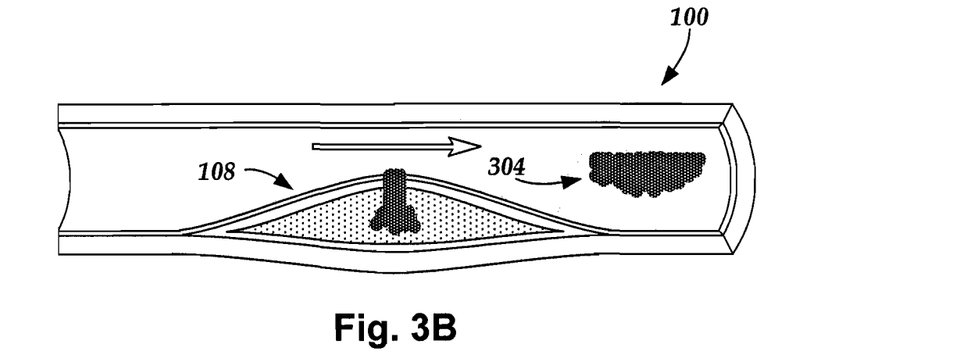
FIG. 3B is a schematic longitudinal cross-section of the portion of the blood vessel shown in FIG. 1 with a detached thrombus.

A thrombus, or a portion of a thrombus, may detach from the rupture of the cap and be transported downstream. FIG. 3B is a schematic longitudinal cross-section of the portion of the blood vessel shown in FIG. 1 with a detached thrombus. In FIG. 3B, the portion 304 of the thrombus (302 in FIG. 3A) is shown detached and transported to a location downstream from the atheroma 108. The detached portion 304 of the thrombus (302 in FIG. 3A) may subsequently occlude the blood vessel 100 downstream from the atheroma, or occlude one or more other blood vessels downstream from the blood vessel 100.

It has been widely assumed by researchers that atheroma morphology is a major determinant of clinical outcome. Atheromas with a large core and a cap <65 µm may be a specific precursor of atheroma rupture due to tissue stress. However, the mechanism of vulnerable atheroma rupture has eluded researchers since ruptures often occur in regions where computational finite element ("FEM") and fluid structure interaction ("FSI") models do not predict maximal stress. For example, it has been shown experimentally that forty percent of cap ruptures occur in the central part of a cap rather than regions of high curvature at the shoulders of the core where FEM models predict maximum tissue stresses.

In at least some embodiments, it is proposed that the rupture of atheromas with caps can be due, at least in part, to stress induced by debonding of one or more microcalcifications the size of a single cell (<50 µm). Microcalcifications can include macrophages and/or smooth muscle cells that have been calcified as a result of apoptosis and are migrating to or from a core. In at least some embodiments, a model is presented for predicting cap rupture based, in part, on the presence of microcalcifications in the cap and the thickness of the cap. Accordingly, the model applies best to the case where the dimensions of a microcalcification are a significant fraction of the cap thickness and where the location of the microcalcification within the cap can be arbitrary. The model indicates that there is a near doubling of the interface stress at the poles of a microcalcification and that this doubling is only modestly affected by the positioning of the microcalcification within the cap thickness. It is thought that microcalcifications in a core are not dangerous from a mechanical standpoint because they reside within a viscous lipid pool that does not support significant tensile stress. The microcalcifications in the core are essentially floating debris without interface stresses.

Prior FEM models have shown that larger-sized calcifications (with a diameter of at least a millimeter) beneath or adjacent to a core, which can be observed by various imaging techniques, such as magnetic resonance imaging ("MRI"), intravascular ultrasound ("IVUS"), and optical coherence tomography ("OCT"), are predicted to be stable. Conversely, microcalcifications (<50 µm) in a cap may cause debonding at the interface between rigid impurities (the microcalcifications), and a thin elastic layer (the cap), because of the large mismatch in hardness of the microcalcifications and the local stress concentrations that develop at the poles of the microcalcifications along the tensile axis as a result of this mismatch.

Figure 4:
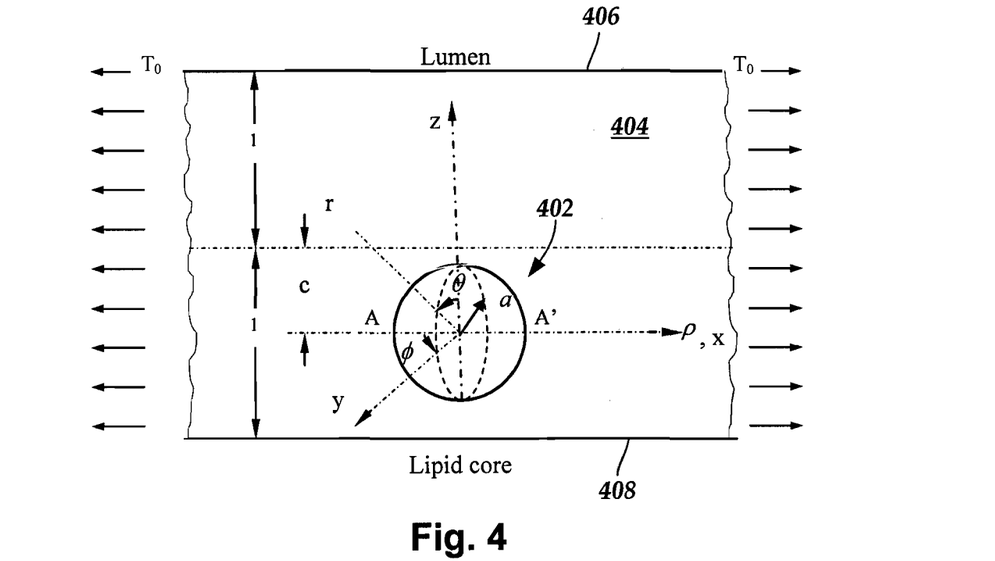
FIG. 4 is a schematic view of a three-dimensional model of a rigid spherical microcalcification in a cap.

FIG. 4 is a schematic view of a three-dimensional model of a rigid spherical microcalcification 402 in a cap 404. In FIG. 4, the model includes the rigid spherical microcalcification 402 eccentrically located in the cap 404 between top (lumen) 406 and bottom (core) 408 boundaries. The circumferential tensile stress in the cap 404 is modeled by unidirectional tension $T_0$ applied at infinity; the top 406 and the bottom 408 boundaries are considered to be stress-free. Let the origin of coordinates be at the center of the microcalcification 402 with the z axis normal to the surfaces. The spherical and cylindrical coordinates are denoted by $(r,\phi,\theta)$ and $(\rho,\phi,z)$ respectively. For convenience, r, z, $\rho$, and all other lengths are made dimensionless by scaling relative to the half-thickness of the tissue layer. In such notation, the upper (lumen) 406 and lower (lipid core) 408 surfaces of the cap 404 are represented respectively by $z=\pm1+c$, where c, the eccentric distance between the origin and the midline of the plate, is <1−a. To solve the problem, the Navier-Lame equations of linear elasticity have been applied for the case of equilibrium with no action-at-a-distance forces:

$$(\lambda+\mu)\nabla(\nabla\cdot u)+\mu\nabla^2 u=0, \quad (1)$$

where u (u,v,w) is the displacement vector, and $\lambda$ and $\mu$ are the Lame constants, the stress-free boundary conditions at $z=\pm1+c$, the perfect bonding conditions at the cap/microcalcification interface at r=a, and the condition that the normal stress in the plate in the x direction tend to a uniform stress $T_0$ as x tends to $\pm\infty$. The mathematical expressions for these boundary conditions are provided below:

Stresses and Displacements in a Fibrous Cap Containing a Perfectly Bonded Rigid Spherical Microcalcification The stress-free boundary conditions at $z=\pm1+c$ are $$\frac{\partial u}{\partial z}+\frac{\partial w}{\partial x}=0,\ \frac{\partial v}{\partial z}+\frac{\partial w}{\partial y}=0, \quad (2)$$

-continued $$\frac{\nu}{1-2\nu}\left(\frac{\partial u}{\partial x}+\frac{\partial v}{\partial y}+\frac{\partial w}{\partial z}\right)+\frac{\partial w}{\partial z}=0.$$

Assuming perfect bonding at the rigid spherical microcalcification/cap interface, one requires u=0 at r=a. (3)

The condition that the normal stress in the plate in the x direction tend to a uniform stress $T_0$ as x tends to $\pm\infty$ is given by $$\lim_{x\to\infty}\left[\frac{\nu}{1-2\nu}\left(\frac{\partial u}{\partial x}+\frac{\partial v}{\partial y}+\frac{\partial w}{\partial z}\right)+\frac{\partial u}{\partial x}-\frac{(1+\nu)T_0}{E}\right]\to 0. \quad (4)$$

1. Stress Functions

A general solution of the equations (1)-(4) is represented as a combination of six harmonic functions $\phi_0$, $\phi_1$, $\phi_2$, $\phi_3$, $\phi_4$, $\lambda_3$. Components of the displacement vector $u(u_x, v_y, w_z)$ are expressed in terms of these functions as follows:

$$2Gu_x = \frac{\partial \phi_0}{\partial x}, \quad 2Gv_y = \frac{\partial \phi_0}{\partial y}, \quad 2Gw_z = \frac{\partial \phi_0}{\partial z} \quad (5)$$

$$2Gu_x = x\frac{\partial \phi_1}{\partial x}-(3-4\nu)\phi_1, \quad 2Gv_y = x\frac{\partial \phi_1}{\partial y}, \quad 2Gw_z = x\frac{\partial \phi_1}{\partial z}$$

$$2Gu_x = y\frac{\partial \phi_2}{\partial x}, \quad 2Gv_y = y\frac{\partial \phi_2}{\partial y}-(3-4\nu)\phi_2, \quad 2Gw_z = y\frac{\partial \phi_2}{\partial z}$$

$$2Gu_x = z\frac{\partial \phi_3}{\partial x}, \quad 2Gv_y = z\frac{\partial \phi_3}{\partial y}, \quad 2Gw_z = z\frac{\partial \phi_3}{\partial z}-(3-4\nu)\phi_3$$

$$2Gu_x = x\frac{\partial \phi_4}{\partial x}, \quad 2Gv_y = y\frac{\partial \phi_4}{\partial y},$$

$$2Gw_z = -x\frac{\partial \phi_4}{\partial z}-y\frac{\partial \phi_4}{\partial z}-4(1-\nu)\phi_4$$

$$2Gu_x = 2\frac{\partial \lambda_3}{\partial y}, \quad 2Gv_y = -2\frac{\partial \lambda_3}{\partial x}, \quad w_z = 0$$

where $$\Delta^2\phi_0 = \Delta^2\phi_1 = \Delta^2\phi_2 = \Delta^2\phi_3 = \Delta^2\phi_4 = \Delta^2\lambda_3 = 0, \quad (6)$$

$$\Delta^2 = \frac{\partial^2}{\partial x^2}+\frac{\partial^2}{\partial y^2}+\frac{\partial^2}{\partial z^2},$$

and $\nu$ and G denote Poisson's ratio and the shear modulus respectively. The displacement and stress fields derived from these harmonic stress functions satisfy the governing equation (1) in the absence of body forces.

2. Solution of the Problem in the Absence of an Inclusion.

First we choose harmonic functions $\phi_0$ and $\phi_3$ in the following form:

$$\phi_0 = \frac{T_0}{4}\frac{1-\nu}{1+\nu}(x^2+y^2-2z^2)+ \quad (7)$$

$$\frac{T_0}{4}(x^2-y^2) = -\frac{T_0}{4}\frac{1-\nu}{1+\nu}r^2P_2(\mu)+\frac{T_0}{12}r^2P_2^2(\mu)\cos(2\phi)$$

$$\phi_3 = -\frac{T_0}{2(1+\nu)}z = -\frac{T_0}{2(1+\nu)}rP_1(\mu),$$

where $\mu=\cos\theta$; $P_n(\mu)$ and $P_n^m(\mu)$ are Legendre functions of the first kind of order n and associated Legendre function of the first kind of order n and degree m, respectively. Substituting expressions (7) for harmonic functions $\phi_0$ and $\phi_3$ into expressions (5) one can calculate the corresponding displacement and stress fields:

$$u_x = \frac{T_0}{E}x, \quad v_y = -\frac{\nu T_0}{E}y, \quad w_z = -\frac{\nu T_0}{E} \quad (8)$$

$$\sigma_x = T_0, \quad \sigma_y = \sigma_z = \tau_{xy} = \tau_{xz} = \tau_{yz} = 0, \quad (9)$$

where E is Young's modulus.

Expressions (8), (9) represent a solution of the problem of a thick plate under uniaxial tension $T_0$ parallel to the x axis in the absence of an inclusion.

Equation (9) shows that this solution gives no traction at the surfaces of the plate $z=\pm 1+c$. The components of the displacement on the inclusion surface are:

$$(u_r)_{r=a} = \frac{T_0 a}{2E}\{((1+\nu)\sin^2\theta-2\nu)+(1+\nu)\sin^2\theta\cos 2\phi\} \quad (10)$$

$$(u_\theta)_{r=a} = \frac{T_0 a}{2E}(1+\nu)\sin\theta\cos\theta(1+\cos 2\phi)$$

$$(u_\phi)_{r=a} = -\frac{T_0 a}{2E}(1+\nu)\sin\theta\sin 2\phi$$

In order to satisfy zero displacement boundary conditions at the microcalcification/cap interface (3) when a microcalcification is present, we construct auxiliary stress functions using suitable harmonic functions such that they would yield no traction on the plate surfaces $$(\sigma_z)_{z=\pm 1+c}=(\tau_{\rho z})_{z=\pm 1+c}=(\tau_{\phi z})_{z=\pm 1+c}=0 \quad (11)$$

and satisfy following boundary conditions at r=a:

$$(u_r)_{r=a} = -\frac{T_0 a}{2E}\{((1+\nu)\sin^2\theta-2\nu)+(1+\nu)\sin^2\theta\cos 2\phi\} \quad (12)$$

$$(u_\theta)_{r=a} = -\frac{T_0 a}{2E}(1+\nu)\sin\theta\cos\theta(1+\cos 2\phi)$$

$$(u_\phi)_{r=a} = \frac{T_0 a}{2E}(1+\nu)\sin\theta\sin 2\phi$$

Expressions (11)-(12) are split into an axisymmetric part which does not depend on $\phi$ and an asymmetric part which is a function of $\phi$.

3. Axisymmetric Solution

First we construct the auxiliary stress functions for the case of a stress distribution which is axisymmetric about the z axis as follows:

$$\phi_0 = T_0\sum_{m=0}^{\infty} A_m \frac{P_m(\mu)}{r^{m+1}}, \quad \phi_3 = T_0\sum_{m=0}^{\infty} B_m \frac{P_m(\mu)}{r^{m+1}} \quad (14)$$

where $A_m$, $B_m$ are unknown coefficients of the spherical stress functions, $P_m(\mu)$ are Legendre functions and $$\phi_0 = T_0\int_0^\infty \psi_1(\lambda) J_0(\lambda\rho)\cosh\lambda z\, d\lambda, \quad (15)$$

$$\phi_3 = T_0\int_0^\infty \lambda\psi_2(\lambda) J_0(\lambda\rho)\sinh\lambda z\, d\lambda$$

$$\phi_0 = T_0\int_0^\infty \psi_1^*(\lambda) J_0(\lambda\rho)\sinh\lambda z\, d\lambda,$$

$$\phi_3 = T_0 \int_0^\infty \lambda \psi_2^*(\lambda) J_0(\lambda\rho) \cosh\lambda z \, d\lambda$$

where $J_0(\lambda\rho)$ is a Bessel function of the first kind of the zero order and $\psi_1(\lambda)$, $\psi_2(\lambda)$, $\psi_1^*(\lambda)$, $\psi_2^*(\lambda)$ are arbitrary cylindrical functions of $\lambda$.

The following integral relation $$\frac{P_n^m(\mu)}{r^{m+1}} = \frac{1}{(m-n)!} \int_0^\infty \lambda^m J_n(\lambda\rho) e^{-\lambda z} d\lambda \quad (z > 0) \tag{16}$$

allows one to express the spherical stress functions (14) in cylindrical coordinates and rewrite the stress-free boundary conditions at $z = \pm 1 + c$ (11) as follows:

$$\left(\frac{\sigma_z}{T_0}\right)_{z=\pm 1+c} = \tag{17}$$

$$\int_0^\infty \lambda^2 \Bigg[ \psi_1(\lambda)\cosh(1 \pm c)\lambda + ((1 \pm c)\lambda\sinh(1 \pm c)\lambda - 2(1-v)$$

$$\cosh(1 \pm c)\lambda)\psi_2(\lambda) \mp \psi_1^*(\lambda)\sinh(1 \pm c)\lambda \mp$$

$$((1 \pm c)\lambda\cosh(1 \pm c)\lambda - 2(1-v)\sinh(1 \pm c)\lambda)\psi_2^*(\lambda) +$$

$$\sum_{m=0}^\infty \left(\frac{A_{2m}}{(2m)!}\lambda^{2m} \pm \frac{A_{2m+1}}{(2m+1)!}\lambda^{2m+1}\right) e^{-(1\pm c)\lambda} +$$

$$\sum_{m=0}^\infty \left(\pm \frac{B_{2m}}{(2m)!}\lambda^{2m-1} \pm \frac{B_{2m+1}}{(2m+1)!}\lambda^{2m+1}\right) \times$$

$$(2(1-v) + (1 \pm c)\lambda) e^{-(1\pm c)\lambda} \Bigg] J_0(\lambda\rho) d\lambda = 0$$

$$\left(\frac{\tau_{\rho z}}{T_0}\right)_{z=\pm 1+c} = \int_0^\infty \lambda^2 \Bigg[ \psi_1(\lambda)\sinh(1 \pm c)\lambda -$$

$$((1-2v)\sinh(1 \pm c)\lambda - (1 \pm c)\lambda\cosh(1 \pm c)\lambda)\psi_2(\lambda) \mp$$

$$\psi_1^*(\lambda)\cosh(1 \pm c)\lambda \mp$$

$$((1-2v)\cosh(1 \pm c)\lambda - (1 \pm c)\lambda\sinh(1 \pm c)\lambda)\psi_2^*(\lambda) -$$

$$\sum_{m=0}^\infty \left(\frac{A_{2m}}{(2m)!}\lambda^{2m} \pm \frac{A_{2m+1}}{(2m+1)!}\lambda^{2m+1}\right) e^{-(1\pm c)\lambda} +$$

$$\sum_{m=0}^\infty \left(\pm \frac{B_{2m}}{(2m)!}\lambda^{2m-1} \pm \frac{B_{2m+1}}{(2m+1)!}\lambda^{2m+1}\right) \times$$

$$((1-2v) + (1 \pm c)\lambda) e^{-(1\pm c)\lambda} \Bigg] J_1(\lambda\rho) d\lambda = 0$$

The next step is to express cylindrical functions $\psi_1$, $\psi_1^*$, $\psi_2$, $\psi_2^*$ in terms of the spherical functions (14) by applying Hankel transforms to the stress free boundary conditions (17) and solving the four linear algebraic equations simultaneously for $\psi_1$, $\psi_1^*$, $\psi_2$, $\psi_2^*$:

$$\psi_1(\lambda) = \frac{1}{F(\lambda)} \sum_{m=0}^\infty \frac{A_{2m}}{(2m)!} \tag{18}$$

$$\lambda^{2m}\big((3-4v-2\lambda)(\sinh 2\lambda \cosh 2\lambda c - 2\lambda) + e^{-2\lambda}(\sinh 2\lambda -$$

$$2\lambda\cosh 2\lambda c) + 2c\lambda\sinh 2\lambda\sinh 2\lambda c\big) + \sum_{m=0}^\infty \frac{A_{2m+1}}{(2m+1)!}$$

$$\lambda^{2m+1}\big((3-4v-2\lambda)(\sinh 2\lambda\sinh 2\lambda c - 2\lambda e^{-2\lambda}\sinh 2\lambda c +$$

$$2c\lambda(\sinh 2\lambda\cosh 2\lambda c + 2\lambda)\big) + \sum_{m=0}^\infty \frac{B_{2m}}{(2m)!}\lambda^{2m-1}\big($$

$$(4(1-v)(1-2v) - 2\lambda^2)\sinh 2\lambda\sinh 2\lambda c +$$

$$4\lambda^2 c((3-4v) + \cosh 2\lambda\cosh 2\lambda c) -$$

$$2\lambda^2 c^2 \sinh 2\lambda\sinh 2\lambda c\big) +$$

$$\sum_{m=0}^\infty \frac{B_{2m+1}}{(2m+1)!} \times \lambda^{2m}\big((4(1-v)(1-2v) - 2\lambda^2)$$

$$(\sinh 2\lambda\cosh 2\lambda c - 2\lambda) +$$

$$4\lambda^2 c(\cosh 2\lambda\sinh 2\lambda c - \lambda) -$$

$$2\lambda^2 c^2 \sinh 2\lambda\cosh 2\lambda c\big)$$

$$\psi_1^*(\lambda) = \frac{1}{F(\lambda)} \sum_{m=0}^\infty \frac{A_{2m}}{(2m)!}\lambda^{2m}\big((3-4v-2\lambda)(\sinh 2\lambda\sinh 2\lambda c - 2\lambda e^{-2\lambda}$$

$$\sinh 2\lambda c + 2\lambda c(\sinh 2\lambda \times \cosh 2\lambda c -$$

$$2\lambda) + \sum_{m=0}^\infty \frac{A_{2m+1}}{(2m+1)!}\lambda^{2m+1}((3-$$

$$4v - 2\lambda)(\sinh 2\lambda\cosh 2\lambda c + 2\lambda) -$$

$$e^{-2\lambda}(\sinh 2\lambda + 2\lambda\cosh 2\lambda c) +$$

$$2\lambda c\sinh 2\lambda\sinh 2\lambda c) + \sum_{m=0}^\infty \frac{B_{2m}}{(2m)!}$$

$$\lambda^{2m-1}\bigg((4(1-v)(1-2v) - 2\lambda^2)$$

$$(\sinh 2\lambda\cosh 2\lambda c + 2\lambda) + 4\lambda^2 c\cosh 2$$

$$\lambda\sinh 2\lambda c - 2\lambda^2 c^2(\sinh 2\lambda\cosh 2\lambda c -$$

$$2\lambda) + \sum_{m=0}^\infty \frac{B_{2m+1}}{(2m+1)!}\lambda^{2m} \times$$

$$2\lambda^2 c^2 \sinh 2\lambda\cosh 2\lambda c\bigg)$$

$$\psi_2(\lambda) = \frac{1}{F(\lambda)}\sum_{m=0}^\infty \frac{2A_{2m}}{(2m)!}\lambda^{2m}(\sinh 2\lambda\cosh 2\lambda c - 2\lambda) + \sum_{m=0}^\infty \frac{2A_{2m+1}}{(2m+1)!}$$

$$\lambda^{2m+1}\sinh 2\lambda\sinh 2\lambda c +$$

$$2c\lambda(\sinh 2\lambda\cosh 2\lambda c + 2\lambda) +$$

$$\sum_{m=0}^\infty \frac{B_{2m}}{(2m)!}\lambda^{2m-1}((3-4v+2\lambda)$$

$$\sinh 2\lambda\sinh 2\lambda c + 2\lambda e^{-2\lambda}\sinh 2\lambda c -$$

$$2\lambda c(\sinh 2\lambda\cosh 2\lambda c - 2\lambda)) +$$

$$\sum_{m=0}^\infty \frac{B_{2m+1}}{(2m+1)!}\lambda^{2m}((3-4v+$$

$$2\lambda) \times (\sinh 2\lambda\cosh 2\lambda c - 2\lambda) -$$

$$e^{-2\lambda}(\sinh 2\lambda - 2\lambda\cosh 2\lambda c) -$$

$$2\lambda c\sinh 2\lambda\sinh 2\lambda c)$$

$$\psi_2^*(\lambda) = \frac{1}{F(\lambda)}\sum_{m=0}^\infty \frac{2A_{2m}}{(2m)!}\lambda^{2m}\sinh 2\lambda\cosh 2\lambda c + \sum_{m=0}^\infty \frac{2A_{2m+1}}{(2m+1)!}$$

-continued
$$\lambda^{2m+1}(\sinh 2\lambda \cosh 2\lambda c + 2\lambda) +$$
$$\sum_{m=0}^{\infty} \frac{B_{2m}}{(2m)!} \lambda^{2m-1}((3-4\nu+2\lambda)(\sinh 2\lambda \cosh 2\lambda c + 2\lambda) + e^{-2\lambda}(\sinh 2\lambda + 2\lambda \cosh 2\lambda c) - 2\lambda c \sinh 2\lambda \sinh 2\lambda c) +$$
$$\sum_{m=0}^{\infty} \frac{B_{2m+1}}{(2m+1)!} \lambda^{2m}((3-4\nu+2\lambda)\sinh 2\lambda \sinh 2\lambda c + 2\lambda e^{-2\lambda}\sinh 2\lambda c - 2\lambda c(\sinh 2\lambda \cosh 2\lambda c + 2\lambda)$$

where $$F(\lambda) = \sinh^2 2\lambda - 4\lambda^2$$

To satisfy remaining boundary conditions at the microcalcification/cap interface (12) one has to express the cylindrical functions (15) in spherical coordinates using following relations:

$$J_\nu(k\rho)\cosh kz = \sum_{n=0}^{\infty} \frac{k^{\nu+2n}}{(2\nu+2n)!} r^{\nu+2n} P_{\nu+2n}^\nu(\mu) \quad (19)$$

$$J_\nu(k\rho)\sinh kz = \sum_{n=0}^{\infty} \frac{k^{\nu+2n+1}}{(2\nu+2n+1)!} r^{\nu+2n+1} P_{\nu+2n+1}^\nu(\mu)$$

The resulting expansions of the cylindrical functions $\phi_0$ and $\phi_3$ (15) are given by $$\phi_0 = T_0 \sum_{n=0}^{\infty} a_n r^n P_n(\mu), \quad (20)$$

$$\phi_3 = T_0 \sum_{n=0}^{\infty} b_n r^n P_n(\mu)$$

where coefficients $a_n$ and $b_n$ are determined by $$a_{2n} = \frac{1}{(2n)!} \int_0^\infty \psi_1(\lambda) \lambda^{2n} d\lambda, \quad (21)$$

$$a_{2n+1} = \frac{1}{(2n+1)!} \int_0^\infty \psi_1^*(\lambda) \lambda^{2n+1} d\lambda,$$

$$b_{2n} = \frac{1}{(2n)!} \int_0^\infty \psi_2(\lambda) \lambda^{2n+1} d\lambda,$$

$$b_{2n+1} = \frac{1}{(2n+1)!} \int_0^\infty \psi_2^*(\lambda) \lambda^{2n+2} d\lambda.$$

Substituting $\psi_1(\lambda), \psi_2(\lambda), \psi_1^*(\lambda), \psi_2^*(\lambda)$ given by (18) into equations (21), one obtains expressions for $a_n$ and $b_n$ can be obtained in terms of the unknown spherical coefficients $A_n, B_n$. These expressions contain integrals with respect to $\lambda$ which have to be evaluated numerically.

Finally, using stress functions (5) and satisfying boundary conditions (10), one can obtain the resulting system for the axisymmetric case $$\sum_{n=0}^{\infty} \left( -(n+1)\frac{A_n}{a^{n+2}} - \frac{(n+3-4\nu)}{2n-1}\frac{B_{n-1}}{a^n} - \frac{(n+1)(n+5-4\nu)}{2n+3}\frac{B_{n+1}}{a^{n+2}} + n\alpha_n a^{n-1} + \frac{n(n-4+4\nu)}{2n-1}\beta_{n-1}a^{n-1} + \frac{(n+1)(n-2+4\nu)}{2n+3}\beta_{n+1}a^{n+1} \right) \quad (22)$$

$$P_n = -\frac{1-2\nu}{3(1+\nu)} aP_0 + \frac{a}{3}P_2$$

$$\sum_{n=1}^{\infty} \left( \frac{A_n}{a^{n+2}} + \frac{(n-4+4\nu)}{2n-1}\frac{B_{n-1}}{a^n} + \frac{(n+5-4\nu)}{2n+3}\frac{B_{n+1}}{a^{n+2}} + \alpha_n a^{n-1} + \frac{n-4+4\nu}{2n-1}\beta_{n-1}a^{n-1} + \frac{n+5-4\nu}{2n+3}\beta_{n+1}a^{n+1} \right) P_n' \sin\theta = \frac{1}{2}aP_2'\sin\theta \quad (23)$$

Equating coefficients of each Legendre function $P_n(\mu)$ in equation (22) or its derivative $P_n'(\mu)$ in equation (23) to zero, one obtains a system of linear equations for the unknown coefficients of the spherical harmonics $A_n, B_n$. The axisymmetric solution of the problem (1)-(4) is determined by truncating and solving this system. After solving for the coefficients, one can calculate the stresses and deformations at any point within the plate.

4. Asymmetric Solution

For the asymmetric problem, the pure shear spherical and cylindrical harmonics are defined by $$\phi_0 = T_0 \sum_{m=2}^{\infty} C_m \frac{P_m^2(\mu)}{r^{m+1}} \cos 2\phi, \quad (24)$$

$$\phi_1 = T_0 \sum_{m=2}^{\infty} C_m \frac{P_m^1(\mu)}{r^{m+1}} \cos\phi,$$

$$\phi_2 = -T_0 \sum_{m=2}^{\infty} D_m \frac{P_m^1(\mu)}{r^{m+1}} \sin\phi,$$

$$\phi_3 = T_0 \sum_{m=2}^{\infty} E_m \frac{P_m^2(\mu)}{r^{m+1}} \cos 2\phi,$$

$$\phi_4 = -T_0 \sum_{m=2}^{\infty} \frac{D_m}{(m-1)} \frac{P_m^2(\mu)}{r^{m+1}} \cos 2\phi$$

$$\phi_0 = T_0 \int_0^\infty \varphi_3(\lambda) J_2(\lambda\rho) \cosh\lambda z \cos 2\phi \, d\lambda, \quad (25)$$

$$\phi_1 = T_0 \int_0^\infty \varphi_4(\lambda) J_1(\lambda\rho) \cosh\lambda z \cos\phi \, d\lambda$$

$$\phi_2 = -T_0 \int_0^\infty \varphi_4(\lambda) J_1(\lambda\rho) \cosh\lambda z \sin\phi \, d\lambda,$$

$$\phi_3 = T_0 \int_0^\infty \lambda \varphi_5(\lambda) J_1(\lambda\rho) \sinh\lambda z \cos 2\phi \, d\lambda$$

$$\lambda_3 = T_0 \int_0^\infty \varphi_6(\lambda) J_2(\lambda\rho) \cosh\lambda z \cos 2\phi \, d\lambda$$

$$\phi_0 = T_0 \int_0^\infty \varphi_3^*(\lambda) J_2(\lambda\rho) \sinh\lambda z \cos 2\phi \, d\lambda,$$

$$\phi_1 = T_0 \int_0^\infty \varphi_4^*(\lambda) J_1(\lambda\rho) \sinh\lambda z \cos\phi \, d\lambda$$

$$\phi_2 = -T_0 \int_0^\infty \varphi_4^*(\lambda) J_1(\lambda\rho) \sinh\lambda z \sin\phi \, d\lambda,$$

$$\phi_3 = T_0 \int_0^\infty \lambda \varphi_5^*(\lambda) J_2(\lambda\rho) \sinh\lambda z \cos 2\phi \, d\lambda$$

$$\lambda_3 = T_0 \int_0^\infty \varphi_6^*(\lambda) J_2(\lambda\rho) \sinh\lambda z \cos 2\phi \, d\lambda,$$

where $C_n$, $D_n$ and $E_n$ are unknown coefficients of the spherical harmonics; $\psi_3(\lambda)$, $\psi_4(\lambda)$, $\psi_5(\lambda)$, $\psi_6(\lambda)$ and $\psi_3^*(\lambda)$, $\psi_4^*(\lambda)$, $\psi_5^*(\lambda)$, $\psi_6^*(\lambda)$ are arbitrary functions.

In a similar procedure to that described in the previous section, one satisfies boundary conditions (11) and (12) by using relations (16) and (19). The final equations for the asymmetric case are $$\sum_{n=2}^{\infty} \left( -(n+1)\frac{C_n}{a^{n+2}} - \frac{5-4v}{3}\frac{D_1}{a^2}\delta_n^{(2)} + \right. \tag{26}$$

$$\frac{2(1-2v)}{n}\frac{D_{n-1}}{a^{n+2}} - \frac{(n-2)(n+3-4v)}{2n-1}\frac{E_{n-1}}{a^n} -$$

$$\frac{(n+3)(n+5-4v)}{2n+3}\frac{E_{n+1}}{a^{n+2}} + n\xi_n a^{n-1} + \frac{n-4+4v}{2n-1}\eta_{n-1}a^{n-1} -$$

$$\frac{n-2+4v}{2n+3}\eta_{n+1}a^{n+1} + \frac{(n-2)(n-4+4v)}{2n-1}\varsigma_{n-1}a^{n-1} +$$

$$\left. \frac{(n+3)(n-2+4v)}{2n+3}\varsigma_{n+1}a^{n+1} + 4k_n a^{n-1} \right) P_n^2(\mu) = -\frac{a}{6}P_2^2$$

$$\sum_{n=2}^{\infty} \left( -\frac{C_n}{a^{n+2}} - \frac{1-2v}{2n+3}\frac{D_{n+1}}{a^{n+2}} + \frac{1-2v}{2n-1}\frac{D_{n-1}}{a^n} - \frac{n-2}{2n-1}\frac{E_{n-1}}{a^n} - \right.$$

$$\frac{n+3}{2n+3}\frac{E_{n+1}}{a^{n+2}} - \xi_n a^{n-1} - \frac{1-2v}{2n-1}\eta_{n-1}a^{n-1} +$$

$$\frac{1-2v}{2n+3}\eta_{n+1}a^{n+1} - \frac{n-2}{2n-1}\varsigma_{n-1}a^{n-1} - \frac{n+3}{2n+3}\varsigma_{n+1}a^{n+1} -$$

$$\left. \frac{n(n-1)+4}{2n-1}k_n a^{n-1} + \frac{(n+3)(n+4)}{2n+3}k_{n+2}a^{n+1} \right) P_n^2(\mu) = \frac{a}{12}P_2^2$$

$$\sum_{n=2}^{\infty} \left( -\frac{(1-2v)(n+1)}{n-1}\frac{D_n}{a^{n+1}} + 4(1-v)\frac{E_n}{a^{n+1}} - 2(1-v)\eta_n a^n + \right.$$

$$\left. 4(1-v)\varsigma_n a^n + n(n+3)k_{n+1}a^n \right) P_n^2(\mu) = 0$$

Equating coefficients of each Legendre function $P_n^2(\mu)$ in equation (26) to zero, one obtains a system of linear equations. The asymmetric solution of equations (1)-(4) is determined by solving the linear simultaneous equations for the parametric coefficients of the spherical harmonics $C_n$, $D_n$, $E_n$. Solving for the coefficients, one can calculate the stresses and deformations corresponding to the asymmetric case at any point within the plate.

5. The Combined Solution

Final expressions for the displacement and stress fields are given by $$u = u_1 + u_2 \cos 2\phi,$$

$$\sigma_i = \sigma_{i1} + \sigma_{i2} \cos 2\phi.$$

where $u_1$, $\sigma_{i1}$ and $u_2$, $\sigma_{i2}$ represent the axisymmetric and the symmetric parts respectively. Although the above boundary value problem is three dimensional, it can be solved analytically without resort to numerical methods.

Figure 5A:
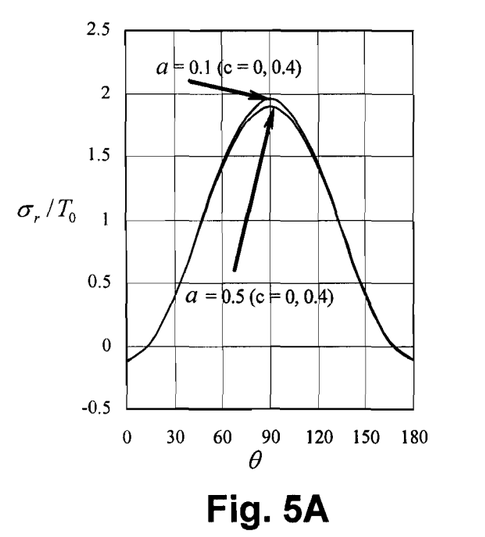
FIG. 5A shows a distribution of calculated radial stress concentration, $\sigma_r/T_0$, at the fibrous-cap/microcalcification interface when the dimensionless radius of the microcalcification is a=0.1 or a=0.5, and the eccentric distance is c=0 or c=0.4 and $\phi=0°$.

The model described above can be used to estimate, determine, or predict the quantitative feasibility of cap rupture occurring due, at least in part, to the debonding of microcalcifications. Accordingly, the model has been used to predict the factor of stress concentration ("FSC") surrounding a rigid spherical microcalcification in the cap. FIG. 5A shows a distribution of calculated radial stress concentration, $\sigma_r/T_0$, at the cap/microcalcification interface when the dimensionless radius of the microcalcification is a=0.1 or a=0.5, and the eccentric distance is c=0 or c=0.4 and $\phi=0°$. FIG. 5A shows that the presence of a rigid spherical microcalcification almost doubles the tension (adhesion stress) at the "poles" A, A' ($\theta=90°$, $\phi=0°$ and $\phi=180°$, in FIG. 4) in the direction of the applied tension $T_0$.

Figure 5B:
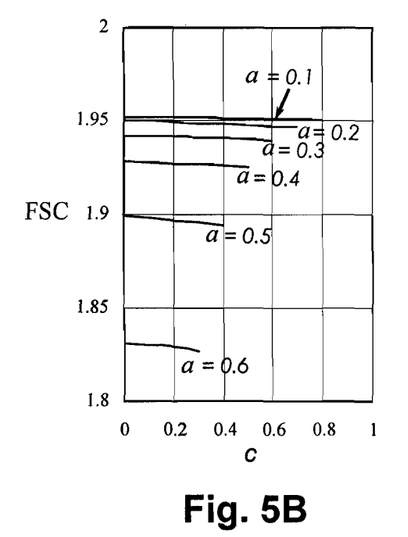
FIG. 5B shows the effect of a free surface on the stress concentration for a=0.1, 0.2, 0.3, 0.4, 0.5, and 0.6.

FIG. 5B is a schematic view of the effect of a free surface on the stress concentration for a=0.1, 0.2, 0.3, 0.4, 0.5, and 0.6. Maximum tensile stresses at the poles A and A' tend to decline slightly as a rigid spherical microcalcification approaches a free surface; the tendency is more noticeable for larger-sized calcifications. It appears that larger-sized calcifications are more stable and that the value of FSC decreases with increasing size. This behavior is similar to the larger-sized calcifications observed in IVUS, discussed above, where FEM calculations predict greater mechanical stability when calcifications with a diameter of at least one millimeter are present. This strengthening occurs since the model does not allow for debonding and the calcification is more rigid than the surrounding material.

Figure 6:
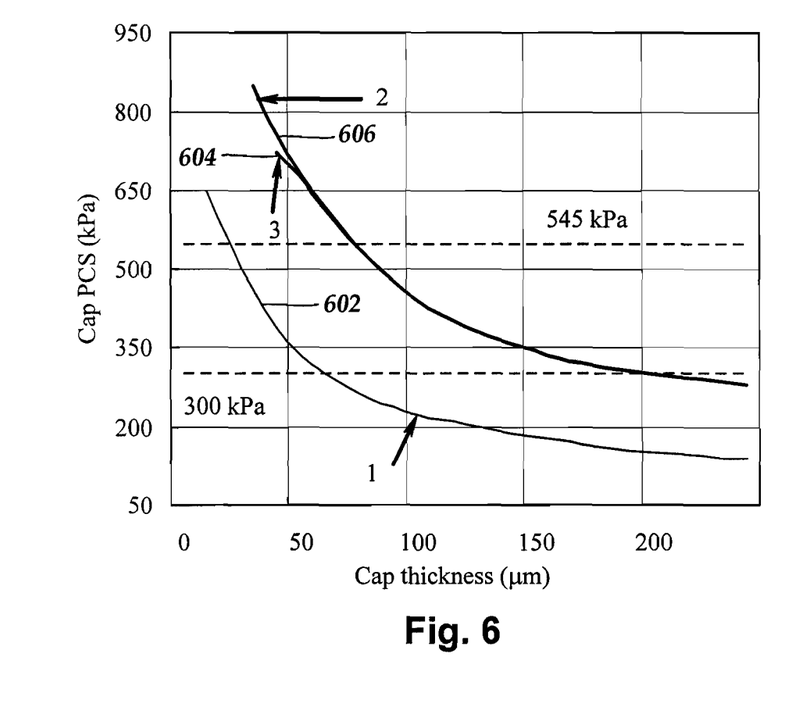
FIG. 6 shows changes in cap peak circumferential stress with cap thickness.

The model of FIG. 4 also can be used to estimate the peak circumferential stress ("PCS") in the cap of an atheroma arising from the presence of a microcalcification. FIG. 6 shows changes in cap PCS with cap thickness. In FIG. 6, the PCS increases exponentially as cap thickness decreases. Finet et al., (Finet, G., Ohayon, J. & Rioufol, G. (2004) *Coron. Artery. Dis.* 15, 13-20) ("Finet") performed FEM calculations to predict the effect of cap thickness on the stability of cap atheroma based on typical in vivo IVUS images. The predictions of Finet's model, shown as Line 1 602 in FIG. 6, show that PCS increases exponentially, and that the average maximum circumferential stress in ruptured plaques is 545 kPa for atheromas with a cap thickness that is ≈25 μm, as shown by Cheng et al. (Cheng, G. C., Loree, H. M., Kamm, R. D., Fishbein, M. C. & Lee, R. T. (1993) *Circulation* 87, 1179-87) ("Cheng"). Finet and Cheng are herein incorporated by reference. These predictions are based on the material properties used in Cheng. The stresses indicated by Line 1 602 are the PCS for a lumen pressure of 14.6 kPa (110 mm Hg) in the absence of a microcalcification.

Line 2 604 and Line 3 606 show PCS increasing when rigid spherical microcalcifications of 10 and 20 μm diameter, respectively, approach to within 5 and 10 μm distances, in that order, from the core of an atheroma. Results of the calculations presented in FIG. 6 provide an explanation of the paradox that most atheroma ruptures occur close to a region of high circumferential tensile stress, defined as a stress of at least 300 kPa, but ruptures are not necessarily located at the points of maximum stress. According to the results shown in FIG. 6, a microcalcification located in an area of high circumferential stress (>300 kPa) in a cap can intensify this stress nearly two-fold to ≈600 kPa when the thickness of the cap is <65 μm. A cap may be in danger of rupturing anytime an average maximum circumferential stress of 545 kPa is exceeded.

Thus, when stress is doubled within a cap by the presence of one or more microcalcifications, the doubling of the stress is more likely to cause a rupture of the cap when the location of the one or more microcalcifications in the cap are in a vulnerable region of the cap, such as a location of high stress (for example, a shoulder of a cap) or a region with a thickness <65 μm. Accordingly, it is possible that the site of rupture of a cap depends on the relative location of both the circumferential stress concentration within the cap and whether one or more microcalcifications are present in the cap.

The model may seem counterintuitive at first because, as discussed above, larger-sized calcifications with a diameter of at least one millimeter have been shown to be stabilizing by FEM calculations. Computational analysis applied to typical ruptured or stable human coronary atheromas reveals that larger-sized calcifications deeper in the intima do not increase cap stress in the atheromas. In contrast to a core, which dramatically increases cap stresses, bulk calcification does not appear to decrease the mechanical stability of a coronary atheroma. Three-dimensional FEM calculations of the longitudinal stress distribution within atheromas based on a simplified axisymmetric geometry suggest that superficial larger-sized calcifications adjacent to a core lead to a decrease in the peak longitudinal stress value at the cap just above the core. The model also predicts that the larger-sized calcifications are more stable and the value of circumferential stress concentration decreases with increasing size. This behavior is similar to the larger-sized calcifications observed in IVUS where FEM calculations predict greater mechanical stability when larger-sized calcifications are present. This strengthening occurs since the theoretical model does not allow for debonding and the calcification is more rigid than the surrounding material. Larger-sized calcifications are also frequently observed beneath or at the edges of cores where the cap is thicker. For these larger-sized calcifications, the stress is also nearly doubled, but the background stress is much lower and even with a two-fold increase in stress, the total stress remains below a threshold stress of 300 kPa.

Typically, failure of a cap due to an increase in stress caused by the presence of a microcalcification does not occur unless there is debonding (failure at the cap/microcalcification interface). While not wishing to be bound by a particular theory, it is thought that the most frequent cause of debonding is the formation of a cavitation bubble at the cap/microcalcification interface, which then rapidly expands. As an example, a circumferential stress of 4091±1199 mm Hg (545±160 kPa) in a ruptured cap is almost equivalent to six atmospheres and, thus, far greater than needed to produce a negative pressure or vacuum at the failure interface.

The presence of microcalcifications in a cap of a ruptured atheroma has been verified using several different in vitro imaging techniques. Confocal laser scanning using an inverted research microscope has been used, along with a calcium-specific stain (Alizarin red S stain), to demonstrate the presence of microcalcifications in atheromas. Additionally, the presence of microcalcifications in a cap of a ruptured atheroma has also been visualized in vitro using micro-computed tomography ("micro-CT"). Both in vitro imaging techniques have shown numerous cellular- and subcellular-level microcalcifications in the cores. However, only a relatively small number of microcalcifications were observed in the caps.

As an example of a confocal imaging method, human coronary segments (obtained from cadavers at autopsy time, less than 12 hours after death) were pressure fixed with 10% formalin and later stained with 2% aqueous solution of Alizarin Red S (SIGMA A5533-25G) at pH 4.2 for 5 minutes (30). After staining, the samples were washed twice with de-ionized $H_2O$ followed by 70% ethanol to remove the excess stain from the tissue. The segments were examined using a confocal laser scanning microscope system manufactured by Leica™ DM IRE2 with an oil immersed objective (index of refraction n=1.4; magnification level 63×). Confocal spectral imaging was used to verify the presence of Alizarin-derived signals with expected emission maxima at 650 nm. The detection window was selected using a Leica™ acousto-optical beam splitter (AOBS) ranged from 645 to 665 nm for these measurements (633 nm HeNe Laser excitation). For reference, interference contrast images were collected using a Leica™ tube optics HC 1×/B apparatus with a focusing Bertrand lens for setting the contrast.

As an example of a micro-CT imaging method, formalin fixed human coronary segments (≈25 mm length, N=24) were obtained from cadavers at autopsy. The segments were scanned using a General Electric® Healthcare eXplore SP Pre-Clinical Specimen micro CT acquisition and analysis system. The coronary samples were kept in PBS at 4° C. and stabilized at room temperature for 30 minutes prior scanning procedure. For image acquisition, x-ray projections were generated from the sample each 0.5° increments of rotation, obtaining 720 consecutive views with maximal 7-µm resolution. For image acquisition, x-ray projections were generated from the sample. Five exposures by projection were used to produce high-contrast, low-noise images. The raw images were corrected for possible pixel defects in the digital detector by using bright and dark fields, and a standard reconstruction algorithm (Feldkamp cone beam) included in the GE® acquisition system was applied to generate three-dimensional volumes from the planar x-ray projections. Densities within the volumes were calibrated by using a phantom containing hydroxyapatite (a main component of bone mineralized phase), air, and water, which was included with each scan.

Initial reconstructions of the whole volumes were carried out at 35-µm voxel resolution. Because of computational limitations to handle digital data sets higher than 800 MB, the digital volumes were sectioned in consecutive volumes of interest consisting of the whole vessel circumference and ≈3 mm in height, which were reconstructed at 7-µm resolution, resulting in eight to nine sections per sample. Density-calibrated images were segmented by using the global threshold method built-in MicroView™ visualization and analysis software (GE® Healthcare; Version 2.1.2). The presence of mineral, soft tissue, lipid, and air in the vessels was distinguished by the high sensitivity of the system to the different densities on each of these compartments. Mineralized tissue particles were investigated on each volumes of interest, and isosurfaces of microcalcifications in the caps of atheroma were rendered by using the MicroView™ software.

Macrophages and smooth muscle cells in a core have been observed to calcify after apoptosis. It is possible that either or both of these cell types may undergo apoptosis and calcification during migration across a cap of an atheroma. The confocal laser scanning microscopy technique discussed above was developed to identify calcium in vitro using Alizarin red S stain. In contrast to histological sectioning, confocal laser scanning microscopy does not require sample dehydration and processing and allows one to study biological materials in their normal hydrated state. Furthermore, measurement of fluorescent reporter group mobility and localization within structures can be observed and used to provide important information regarding the biochemical, biophysical, and structural status of microcalcifications and their context within a blood vessel wall.

The three-dimensional nondestructive in vitro micro-CT imaging technique, described above, facilitates a systematic analysis of intact and unprocessed coronary artery segments. Micro CT imaging provides an accurate characterization of atheroma morphology due to the difference in density between air, soft tissue, lipid, and mineral. In contrast to histologic processing, which includes fixation, dehydration, and some degree of decalcification before paraffin embedding to allow sectioning, micro CT imaging can be performed in unprocessed coronary arteries. This prevents mechanical and physiochemical artifacts, such as shrinkage of the specimen, and retains true calcification morphology because no decalcification is involved.

Another problem with histological analysis is the difficulty of obtaining adjacent sections and avoiding distortion during the sectioning process. Histologic microscopy also does not provide three-dimensional information and as a destructive technique, is limited to a small number of two-dimensional sections. With micro CT, a complete digital data set of the whole vessel is available. Using tomographic reconstruction algorithms, three-dimensional images of a vessel wall can be generated that allow total stereoscopic visualization of the three-dimensional microarchitecture.

A variety of in vivo imaging techniques can be used to determine the presence of microcalcifications in caps of atheromas. The resolving power of a suitable in vivo imaging technique may vary. For example, an in vivo imaging technique may have a resolution of at least 50 micrometers, at least forty micrometers, at least thirty micrometers, at least twenty micrometers, at least ten micrometers, at least five micrometers, or at least one micrometer. As will be recognized, other resolutions may also be used. The penetration depth of the in vivo imaging technique should be suitable to detect microcalcifications. For example, an in vivo imaging technique may have a penetration depth of at least one-half millimeter, at least one millimeter, at least two millimeters, at least three millimeters, at least four millimeter, or at least five millimeters. As will be recognized, other penetration depths may also be used. In a preferred embodiment, an in vivo imaging technique is sensitive to calcium.

In at least some embodiments, a high-frequency ultrasound is used. A high-frequency ultrasound may have a variety of different frequencies. For example, a frequency of at least 100 MHz, at least 120 MHz, at least 140 MHz, at least 160 MHz, or at least 180 MHz. In a preferred embodiment, an intravascular high-frequency ultrasound is used with a frequency of at least 180 MHz, a resolution of at least 5 μm, and a penetration depth of at least one millimeter. The intravascular high-frequency ultrasound can be mounted on a catheter and inserted into one or more blood vessels of a patient and used to image microcalcifications in caps of atheromas. Ultrasound typically has sufficient contrast to distinguish calcium from soft tissue, air, and liquids, as desired for determining the presence of microcalcifications in a cap of an atheroma. In at least some embodiments, other suitable in vivo imaging techniques can be used that are capable of a resolution of at least 50 μm and a penetration of at least one millimeter, such as OCT, high-resolution MRI, and the like. In at least some embodiments, combinations of two or more different in vivo imaging techniques can be used together to determine the presence of microcalcifications in caps. Additionally, in at least some embodiments a contrast agent can be used to enhance visibility of microcalcifications. Generally, the contrast agent should be biocompatible and the uptake into the vessel walls should be sufficiently rapid to permit imaging within a desired time frame after administration of the contrast agent. In one embodiment, Alazarin red S stain is used in conjunction with one or more in vivo imaging techniques. In at least some embodiments, one or more techniques for determining tissue composition, such as infrared spectroscopy and the like, can be used in conjunction with one or more in vivo imaging techniques.

In at least some embodiments, one or more screening methodologies may be used to identify atheromas that are suspected as being vulnerable and to locate their positions prior to undergoing an in vivo imaging technique to determine whether the identified atheromas include at least one microcalcification. Any suitable in vivo imaging technique can be used for screening that is capable of imaging atheromas in blood vessels, including the intravascular high-frequency ultrasound, OCT, and high-resolution MRI imaging techniques mentioned above, as well as other in vivo imaging techniques such as angiography, IVUS, computed tomography, MRI, and the like. Additionally, other screening techniques may be utilized such as infrared spectroscopy, pressure tests, and the like.

In at least some embodiments, when it has been determined by using an in vivo imaging technique that a patient has an atheroma with one or more microcalcifications on the cap, the risk of rupture of the cap can be estimated, determined, or predicted based on several different variables, including the presence of one or more microcalcifications in a cap and the thickness of the cap. Additionally, in some embodiments other variables are included in the prediction to estimate, determine, or predict the risk of rupture, such as cap curvature, material properties of the cap, the number of microcalcifications, the size of the one or more microcalcifications, the shape of the one or more microcalcifications, the size of core, and the location of the microcalcification within the cap. Once values are determined based on the in vivo imaging technique, the risk of rupture can be determined using a quantitative technique designed to estimate the risk of rupture of the cap. In at least some embodiments, a finite-element model of the mechanical stress in a blood vessel wall is determined based on the geometric information derived from the in vivo imaging. In one embodiment, a calculation of stress is based on an analytic expression that estimates or models a stress-profile in a cap using one or more of the variables listed above, such as cap thickness, microcalcification size, and microcalcification location. In a preferred embodiment, image segmentation methods, such as Mimics (three-dimensional image processing and editing software based on scanner data and developed by Materialise™) computes from a volumetric image a three-dimensional finite-element ("FE") mesh describing boundary of multiple components such as the core, microcalcifications, and fibrotic tissue. The FE mesh is used by an FE solver, such as Abaqus (finite element analysis software, available through Simulia™), to compute three-dimensional stresses in the artery and, in particular, in a cap containing one or more microcalcifications. The stresses are then compared against known rupture thresholds to determine the likelihood of rupture of the cap.

Detection of microcalcifications or the determinations of a risk of rupture may suggest the initiation of a treatment regime. The patient can be treated to either attempt to prevent rupture of a cap or to reduce damage to the patient caused by imminent rupture of a cap, or both. Various different treatment options are possible and may be decided based on many different clinical criteria which may or may not be individualized to the specific needs of the patient. A few common generic treatment options include one or more of: lowering patient cholesterol level, lowering patient blood pressure, prescribing blood thinners to the patient, performing angioplasty on the patient, and fitting the patient with one or more stents (either drug-eluting or non-drug-eluting), surgery (such as an atherectomy), regenerative tissue engineering, regenerative stem cell treatment, drug-eluting scaffolds, and the like.

Figure 7:
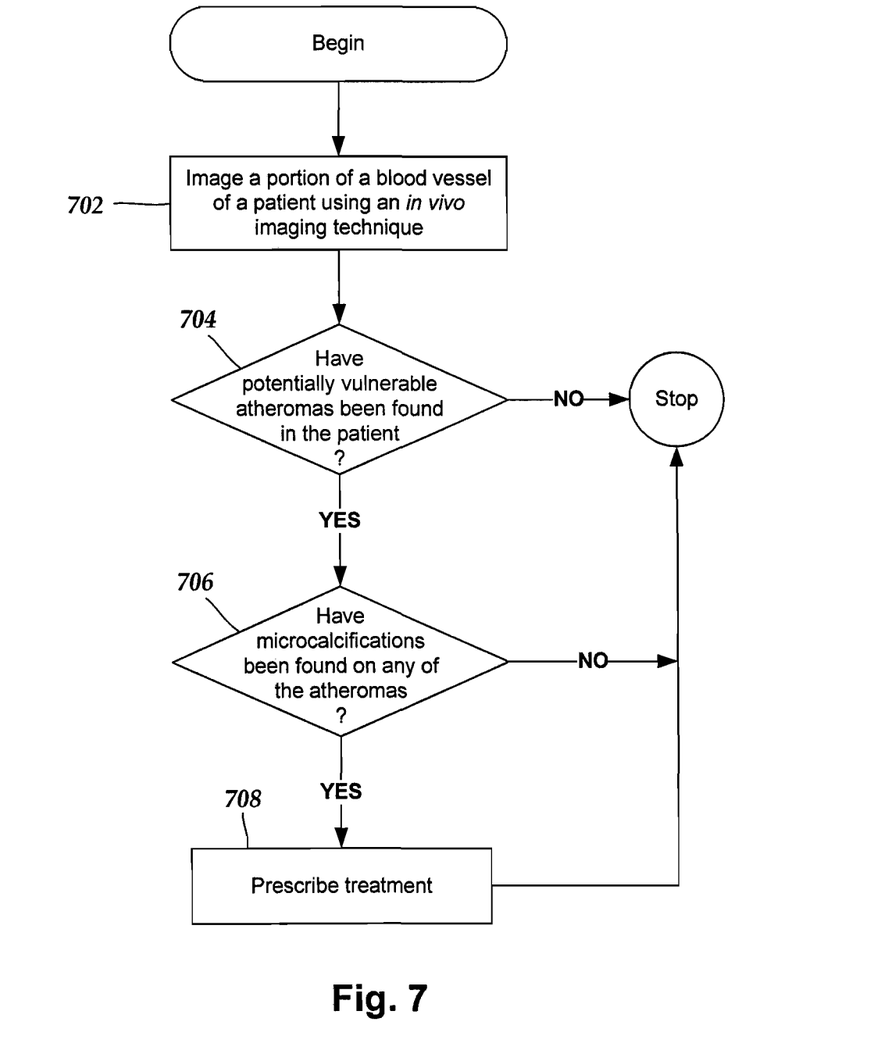
FIG. 7 illustrates a flow diagram showing one embodiment of exemplary steps used for determining the risk of cap rupture and subsequent treatment, according to the invention.

FIG. 7 illustrates a flow diagram showing one embodiment of exemplary steps used for determining the risk of cap rupture and subsequent treatment, according to the invention. In step 702, a portion of a blood vessel of a patient is imaged for detecting potentially vulnerable atheromas using an in vivo imaging technique. When, in step 704, no potentially vulnerable atheromas are found in the patient, the process stops. Otherwise, when one or more potentially vulnerable atheromas are found in the patient, control is passed to step 706 where a portion of a blood vessel of a patient is imaged for detecting microcalcifications on any of the atheromas using an in vivo imaging technique. When, in step 706, no microcalcifications are detected on any of the atheromas, the process stops. Otherwise, when one or more microcalcifications are observed on one or more of the atheromas, a treatment is prescribed (step 708). After, or during, treatment, the process may be repeated one or more times to monitor the atheromas. Additionally, one or more screening methodologies can be used to locate the portion of the blood vessels of the patient to be imaged.

Figure 8:
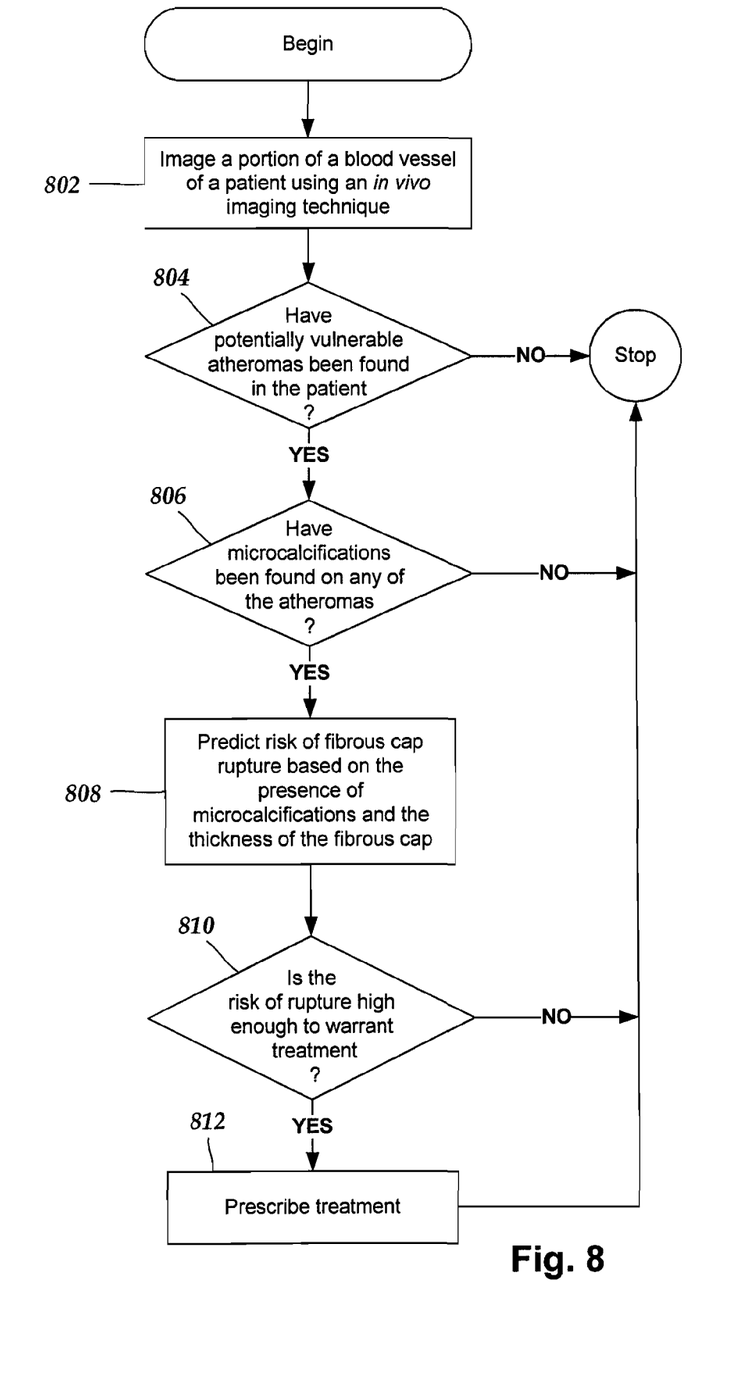
FIG. 8 illustrates a flow diagram showing one embodiment of exemplary steps used for determining the risk of cap rupture and subsequent treatment, according to the invention.

FIG. 8 illustrates a flow diagram showing another embodiment of exemplary steps used for determining the risk of cap rupture and subsequent treatment, according to the invention. In step 802, a portion of a blood vessel of a patient is imaged for detecting potentially vulnerable atheromas using an in vivo imaging technique. When, in step 804, no potentially vulnerable atheromas are found in the patient, the process stops. Otherwise, when one or more potentially vulnerable atheromas are found in the patient, control is passed to step 806 where a portion of a blood vessel of a patient is imaged for detecting microcalcifications on any of the atheromas using an in vivo imaging technique. When, in step 806, no microcalcifications are detected on any of the atheromas, the process stops. Otherwise, when one or more microcalcifications are observed on one or more of the atheromas, a risk of rupture of one or more of the atheromas is predicted (step 808) based, at least, on the presence of one or more microcalcifications and the thickness of the cap. When, in step 810, the risk of rupture is determined to not be high enough to warrant treatment, the cap-management process stops. Otherwise, when the risk of rupture is determined to be high enough to warrant treatment, a treatment is prescribed (step 812). After, or during, treatment, the process may be repeated one or more times to monitor the atheromas. Additionally, one or more screening methodologies can be used to locate the portion of the blood vessels of the patient to be imaged.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A method comprising:
    imaging a portion of a blood vessel of a patient in vivo, said portion comprising a fibrous cap of an atheroma, wherein said imaging utilizes an in vivo imaging device with a resolution level of at least fifty micrometers and capable of detecting a microcalcification in a fibrous cap of an atheroma;
    determining from the imaging the presence of at least one microcalcification within the fibrous cap of the atheroma wherein the at least one microcalcification has a diameter of no less than five and no more than fifty micrometers, the size and location of the at least one microcalcification within the cap, and the thickness of the fibrous cap, wherein the at least one microcalcification has a diameter of no less than five and no more than fifty micrometers; and
    predicting a risk of rupture of the cap based on the determined features of:
    the presence of at least one microcalcification having a diameter of no less than five and no more than fifty micrometers within the fibrous cap of the atheroma wherein the presence of the at least one microcalcification existing within the fibrous cap correlates with an increased risk of rupture;
    the size of the at least one microcalcification;
    the location of the at least one microcalcification within the cap; and
    the thickness of the fibrous cap.

2. The method of claim 1, wherein imaging a portion of a blood vessel comprises imaging the portion of the blood vessel using said imaging device is a high-frequency ultrasound imaging device.

3. The method of claim 2, wherein imaging a portion of a blood vessel comprises imaging the portion of the blood vessel using said high-frequency ultrasound imaging device has a frequency of at least one hundred Megahertz.

4. The method of claim 2, wherein imaging a portion of a blood vessel comprises imaging the portion of the blood vessel using said high-frequency ultrasound device is mounted on a catheter configured and arranged for insertion into the blood vessel of the patient.

5. The method of claim 2, wherein imaging a portion of a blood vessel further comprises determining the tissue composition of the portion of the blood vessel using infrared spectroscopy.

6. The method of claim 1, wherein the imaging a portion of a blood vessel comprises imaging the portion of the blood vessel is performed while a contrast agent is in at least a portion of the patient to be imaged.

7. The method of claim 1, wherein the predicted risk of rupture of the fibrous cap is quantitatively assessed by using a finite element model to construct a stress profile of the fibrous cap.

8. The method of claim 1, further comprising treating the patient based on the prediction of the risk of rupture of the fibrous cap to prevent rupture of the fibrous cap or to reduce damage to the patient caused by rupture of the fibrous cap.

9. The method of claim 1, wherein the determining step is performed by a processor an image of the blood vessel from the in vivo imaging device is received and used by a processor to determine whether the blood vessel contains at least one microcalcification within the fibrous cap, the size and the location of the at least one microcalcification within the cap, and the thickness of the fibrous cap.

10. The method of claim 1, further comprising determining the relative location of a detected microcalcification within the cap with respect to an area having circumferential stress of at least 300 kPa or to an area having a thickness of less than 65 μm.

11. The method of claim 1, wherein the imaging step is performed on comprises imaging a longitudinal cross-section portion of the blood vessel.

12. The method of claim 1, wherein the determining determines whether the blood vessel includes said at least one microcalcification comprises a plurality of microcalcifications having a diameter of no less than five and no more than fifty micrometers.

13. The method of claim 1, wherein the determining step determines whether the blood vessel includes at least one microcalcification within the fibrous cap of the atheroma wherein said at least one microcalcification has a diameter of no less than 5 and no more than 25 micrometers, the size and location of the at least one microcalcification within the cap, and the thickness of the fibrous cap, and the risk of rupture is predicted based on:
    the presence of at least one microcalcification having a diameter of no less than 5 and no more than 25 micrometers within the fibrous cap of the atheroma wherein the presence of the at least one microcalcification existing within the fibrous cap correlates with an increased risk of rupture;
the size of the at least one microcalcification;
the location of the at least one microcalcification within the cap; and
the thickness of the fibrous cap.

* * * * *